US011430230B2

(12) United States Patent
Noda et al.

(10) Patent No.: US 11,430,230 B2
(45) Date of Patent: Aug. 30, 2022

(54) STORAGE DEVICE AND EXCITEMENT SUPPRESSION DEVICE

(71) Applicant: Pioneer Corporation, Tokyo (JP)

(72) Inventors: Yasuyuki Noda, Kawagoe (JP); Hiroshi Yamazaki, Kawagoe (JP)

(73) Assignee: PIONEER CORPORATION, Tokyo (JP)

( * ) Notice: Subject to any disclaimer, the term of this patent is extended or adjusted under 35 U.S.C. 154(b) by 134 days.

(21) Appl. No.: 16/958,574

(22) PCT Filed: Dec. 21, 2018

(86) PCT No.: PCT/JP2018/047182
§ 371 (c)(1),
(2) Date: Jun. 26, 2020

(87) PCT Pub. No.: WO2019/131485
PCT Pub. Date: Jul. 4, 2019

(65) Prior Publication Data

US 2021/0064895 A1 Mar. 4, 2021

(30) Foreign Application Priority Data

Dec. 27, 2017 (JP) ............................ JP2017-251698

(51) Int. Cl.
*G06V 20/59* (2022.01)
*B60W 60/00* (2020.01)
(Continued)

(52) U.S. Cl.
CPC ........... *G06V 20/597* (2022.01); *B60W 40/09* (2013.01); *B60W 60/005* (2020.02); *G06K 9/6232* (2013.01); *B60W 2040/0872* (2013.01)

(58) Field of Classification Search
None
See application file for complete search history.

(56) References Cited

U.S. PATENT DOCUMENTS

2013/0041564 A1* 2/2013 Doi .................... B60W 50/087 701/70
2014/0139341 A1* 5/2014 Green .................... A61B 5/163 340/576
(Continued)

FOREIGN PATENT DOCUMENTS

DE 101 52 852 A1 5/2003
DE 10 2016 207447 A1 11/2017
(Continued)

OTHER PUBLICATIONS

International Search Report for related PCT App No. PCT/JP2018/047182 dated Mar. 19, 2019, 3 pgs.
(Continued)

*Primary Examiner* — Santiago Garcia
(74) *Attorney, Agent, or Firm* — Procopio, Cory, Hargreaves & Savitch LLP

(57) ABSTRACT

The storage device according to the present invention is characterized by comprising: a feature amount detection unit that detects feature amounts related to actions of an occupant in a moving body; an excitement degree acquisition unit that acquires excitement degree information indicating the degree of excitement of the occupant when the feature amounts have been detected; and a feature amount storage unit that calculates, on the basis of the feature amounts and the excitement degree information, a first corresponding feature amount corresponding to a first excitement degree of the degree of excitement, and stores the first corresponding feature amount in association with the first excitement degree.

4 Claims, 12 Drawing Sheets

(51) Int. Cl.

| | |
|---|---|
| ***B60W 40/09*** | (2012.01) |
| ***G06K 9/62*** | (2022.01) |
| ***B60W 40/08*** | (2012.01) |

(56) References Cited

U.S. PATENT DOCUMENTS

| | | | | |
|---|---|---|---|---|
| 2014/0218187 | A1* | 8/2014 | Chun | B60K 28/066 340/439 |
| 2016/0052394 | A1 | 2/2016 | Yamada | |
| 2016/0355190 | A1* | 12/2016 | Omi | G06N 5/04 |
| 2017/0155867 | A1* | 6/2017 | Yokota | H04N 5/44504 |
| 2018/0053093 | A1* | 2/2018 | Olabiyi | B60W 40/09 |
| 2018/0053102 | A1* | 2/2018 | Martinson | G08G 1/09623 |
| 2018/0096699 | A1* | 4/2018 | Shintani | B60W 50/08 |
| 2019/0143989 | A1* | 5/2019 | Oba | G08G 1/04 701/70 |
| 2020/0207358 | A1* | 7/2020 | Katz | G06F 3/017 |

FOREIGN PATENT DOCUMENTS

| | | | |
|---|---|---|---|
| EP | 3 057 091 | A1 | 8/2016 |
| JP | 2009018047 | A | 1/2009 |
| JP | 2010167014 | A | 8/2010 |
| JP | 2015153048 | A | 8/2015 |
| JP | 2015231828 | A | 12/2015 |
| JP | 2016045705 | A | 4/2016 |

OTHER PUBLICATIONS

Extended European Search Report, dated Aug. 27, 2021, from European Patent Application No. 18894933.3, 8 pages.

Office Action dated Feb. 9, 2021 in counterpart JP Patent Application No. 2019-561633, 6 pages.

* cited by examiner

T1

| DATA ID | CONTENT NAME | AUTOMATIC DRIVING LEVEL | EVALUATED EXCITEMENT DEGREE | FEATURE AMOUNT (HEAD) | FEATURE AMOUNT (HAND) | FEATURE AMOUNT (FOOT) | FEATURE AMOUNT (VOICE) |
|---|---|---|---|---|---|---|---|
| 1 | AAAA | 0 | 1 | 0.10 | 0.20 | 0.00 | 0.20 |
| 2 | BBBB | 0 | 3 | 0.40 | 0.30 | 0.10 | 0.60 |
| 3 | CCCC | 0 | 2 | 0.20 | 0.20 | 0.20 | 0.40 |
| 4 | DDDD | 1 | 1 | 0.15 | 0.20 | 0.30 | 0.25 |
| 5 | EEEE | 1 | 2 | 0.35 | 0.30 | 0.20 | 0.45 |
| 6 | FFFF | 2 | 2 | 0.35 | 0.30 | 0.20 | 0.65 |
| 7 | GGGG | 3 OR MORE | 1 | 0.40 | 0.30 | 0.20 | 0.30 |
| 8 | HHHH | 3 OR MORE | 3 | 0.80 | 0.80 | 0.70 | 0.90 |
| 9 | IIII | 2 | 3 | 0.30 | 0.40 | 0.20 | 0.70 |
| 10 | JJJJ | 2 | 2 | 0.50 | 0.80 | 0.50 | 0.45 |
| 11 | KKKK | 1 | 3 | 0.80 | 1.00 | 0.80 | 0.50 |
| ... | ... | ... | ... | ... | ... | ... | ... |

| EXCITEMENT DEGREE | REFERENCE FEATURE AMOUNT (HEAD) | REFERENCE FEATURE AMOUNT (HAND) | REFERENCE FEATURE AMOUNT (FOOT) | REFERENCE FEATURE AMOUNT (VOICE) |
|---|---|---|---|---|
| 1 | 0.25 | 0.25 | 0.20 | 0.30 |
| 2 | 0.50 | 0.35 | 0.30 | 0.50 |
| 3 | 0.60 | 0.45 | 0.45 | 0.70 |

| AUTOMATIC DRIVING LEVEL | EXCITEMENT DEGREE | REFERENCE FEATURE AMOUNT (HEAD) | REFERENCE FEATURE AMOUNT (HAND) | REFERENCE FEATURE AMOUNT (FOOT) | REFERENCE FEATURE AMOUNT (VOICE) |
|---|---|---|---|---|---|
| 0 | 1 | 0.15 | 0.10 | 0.00 | 0.20 |
| 0 | 2 | 0.20 | 0.15 | 0.05 | 0.40 |
| 0 | 3 | 0.30 | 0.25 | 0.10 | 0.60 |
| 1 | 1 | 0.15 | 0.10 | 0.10 | 0.25 |
| 1 | 2 | 0.20 | 0.10 | 0.20 | 0.45 |
| 1 | 3 | 0.30 | 0.10 | 0.30 | 0.65 |
| 2 | 1 | 0.20 | 0.30 | 0.20 | 0.30 |
| 2 | 2 | 0.45 | 0.40 | 0.30 | 0.50 |
| 2 | 3 | 0.60 | 0.50 | 0.40 | 0.70 |
| 3 OR MORE | 1 | 0.50 | 0.50 | 0.50 | 0.30 |
| 3 OR MORE | 2 | 0.70 | 0.70 | 0.70 | 0.60 |
| 3 OR MORE | 3 | 0.90 | 0.90 | 0.90 | 0.90 |

FIG.6

STORAGE DEVICE AND EXCITEMENT SUPPRESSION DEVICE

CROSS-REFERENCE TO RELATED APPLICATIONS

This application is a U.S. National Stage entry of PCT Application No: PCT/JP2018/047182 filed Dec. 21, 2018, which claims priority to Japanese Patent Application No. 2017-251698 filed Dec. 27, 2017, the contents of which are incorporated herein by reference.

TECHNICAL FIELD

The present invention relates to a storage device, and relates to, for example, a storage device configured to store information on an excitement degree of a user and an excitement suppression device using the same.

BACKGROUND ART

Conventionally there has been proposed a terminal device that compares information on a beat of a musical composition with a detection result of a user's movement, determines whether the user moves his/her body according to the musical composition or not, and stores the information on the musical composition and the information indicative of the determination result of whether the body is moving or not in association (Patent Document 1).

Patent Document 1: Japanese Patent No. 6055659

DISCLOSURE OF THE INVENTION

Problems to be Solved by the Invention

For example, for a moving body, such as an automobile, a driver responsible for controlling the moving body is preferred not to be in an excessively excited state. Therefore, the excited state of the driver is preferably determinable. However, the terminal device disclosed in Patent Document 1 only determines whether a user moves according to a musical composition when the musical composition is played or not and stores the result. Therefore, an exemplary problem includes that it is difficult to accurately determine whether the user is currently in the excited state or not by the terminal device disclosed in Patent Document 1 and the information obtained by it.

The present invention has been made in consideration of the above-described points, and it is an object of the present invention to provide a storage device and an excitement degree suppression device for supporting driving of a driver by, for example, effectively controlling an excited state of the driver of a moving body.

Solutions to the Problems

BRIEF DESCRIPTION OF THE DRAWINGS

FIG. 4 is a drawing illustrating an exemplary excitement degree data table.

FIG. 5 is an exemplary reference value table.

FIG. 6 is an exemplary reference value table.

DESCRIPTION OF PREFERRED EMBODIMENTS

Figure 1:
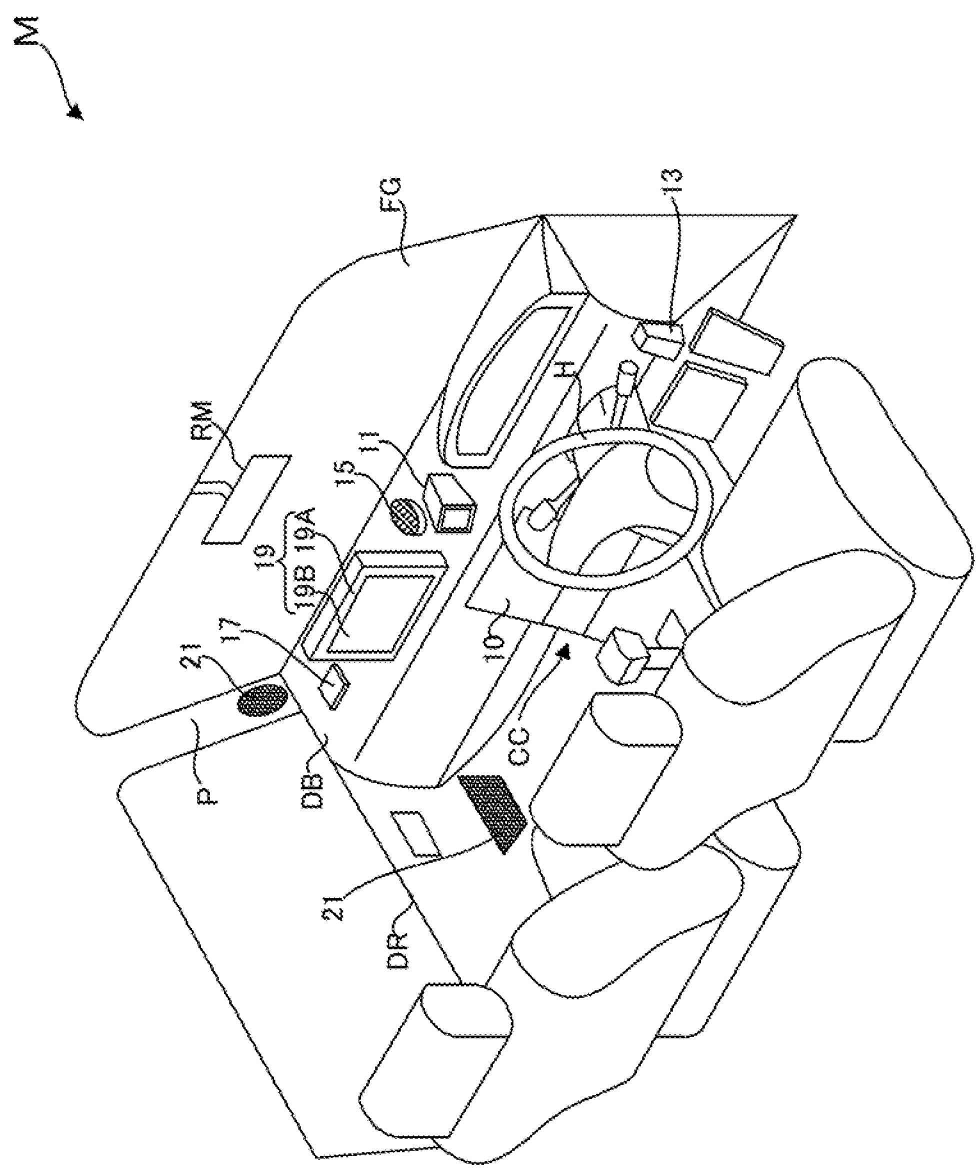
FIG. 1 is a perspective view of a front seat part of an automobile to which an excitement degree control device as Embodiment 1 of the present invention is mounted.

The following describes preferred embodiments of the present invention. However, they may be appropriately modified and combined. In the following description and attached drawings, descriptions will be given while identical reference numerals designate substantially identical or equivalent parts. In the following description, descriptions will be given while a video includes a moving image and a still image.

Embodiment 1

The following describes an excitement degree suppression device 10 as Embodiment 1 of the present invention by referring to the accompanying drawings. In Embodiment 1, a description will be given with an embodiment where an excitement degree control device 10 is mounted to an automobile M.

FIG. 1 is a drawing illustrating an exemplary front seat part of the automobile M as a moving body to which the excitement degree control device 10 is mounted. FIG. 1 illustrates a case where the excitement degree control device 10 is mounted to a center console portion of the front seat of the automobile M as a mounting example.

An upper body camera 11 as an occupant photographing unit is a camera configured to photograph an upper body of an occupant of the automobile M. The upper body camera 11 is disposed on, for example, a dashboard DB, and oriented so as to be capable of photographing a driver on a driver's seat. The upper body camera 11 only needs to be disposed at a position where a state of a movement and the like of the upper body of the occupant can be photographed. For example, the upper body camera 11 may be disposed to an inside rear view mirror RM, or disposed at an upper end of a windshield FG or a ceiling at the proximity of the upper end.

The upper body camera 11 is communicatively connected to the excitement degree control device 10, and configured to transmit a signal of a taken video to the excitement degree control device 10.

A lower body camera 13 is a camera configured to photograph a lower body, for example, feet, of the occupant of the automobile. The lower body camera is disposed on, for example, a surface of the dashboard DB and a side portion of a steering wheel H, and is oriented so as to be capable of photographing the driver's feet. The lower body camera 13 is communicatively connected to the excitement degree control device 10, and configured to transmit a signal of a taken video to the excitement degree control device 10.

A microphone 15 is a microphone device that receives a sound inside the automobile, and disposed on, for example, the dashboard DB. The microphone 15 may be disposed anywhere, for example, at the inside rear view mirror RM or the steering wheel, insofar as the sound inside the automobile can be received. The microphone 15 is communicatively connected to the excitement degree control device 10, and configured to transmit a signal of the collected sound to the excitement degree control device 10.

The upper body camera 11, the lower body camera 13, and the microphone 15 are defined as feature amount detection units to detect a feature amount on an action of the occupant.

A GPS receiver 17 is a device that receives a signal (GPS signal) from a Global Positioning System (GPS) satellite. The GPS receiver 17 is disposed on, for example, the dashboard DB. The GPS receiver 17 may be disposed anywhere insofar as the GPS signal can be received. The GPS receiver 17 is communicatively connected to the excitement degree control device 10, and configured to transmit the received GPS signal to the excitement degree control device 10.

A touch panel 19 is a touch panel monitor, for example, where a display 19A, such as a liquid crystal display, configured to display a video is combined with a touchpad 19B. The touch panel 19 is disposed on, for example, the dashboard DB. The touch panel 19 only needs to be disposed at a position visually perceivable by the driver and reached by the driver with his/her hand. For example, the touch panel 19 may be mounted to a center console CC inside the dashboard DB.

The display 19A is communicatively connected to the excitement degree control device 10, and configured to perform a screen display based on a control by the excitement degree control device 10. The touch pad 19B is configured to transmit a signal that indicates an input operation to the touch pad 19B accepted from a user to the excitement degree control device 10.

A speaker 21 is disposed on, for example, a room interior side of an A pillar P or a door DR. The speaker 21 is communicatively connected to the excitement degree control device 10, and configured to emit sounds, such as music and voice, based on the control by the excitement degree control device 10.

[1. System Configuration and Operation]

Figure 2:
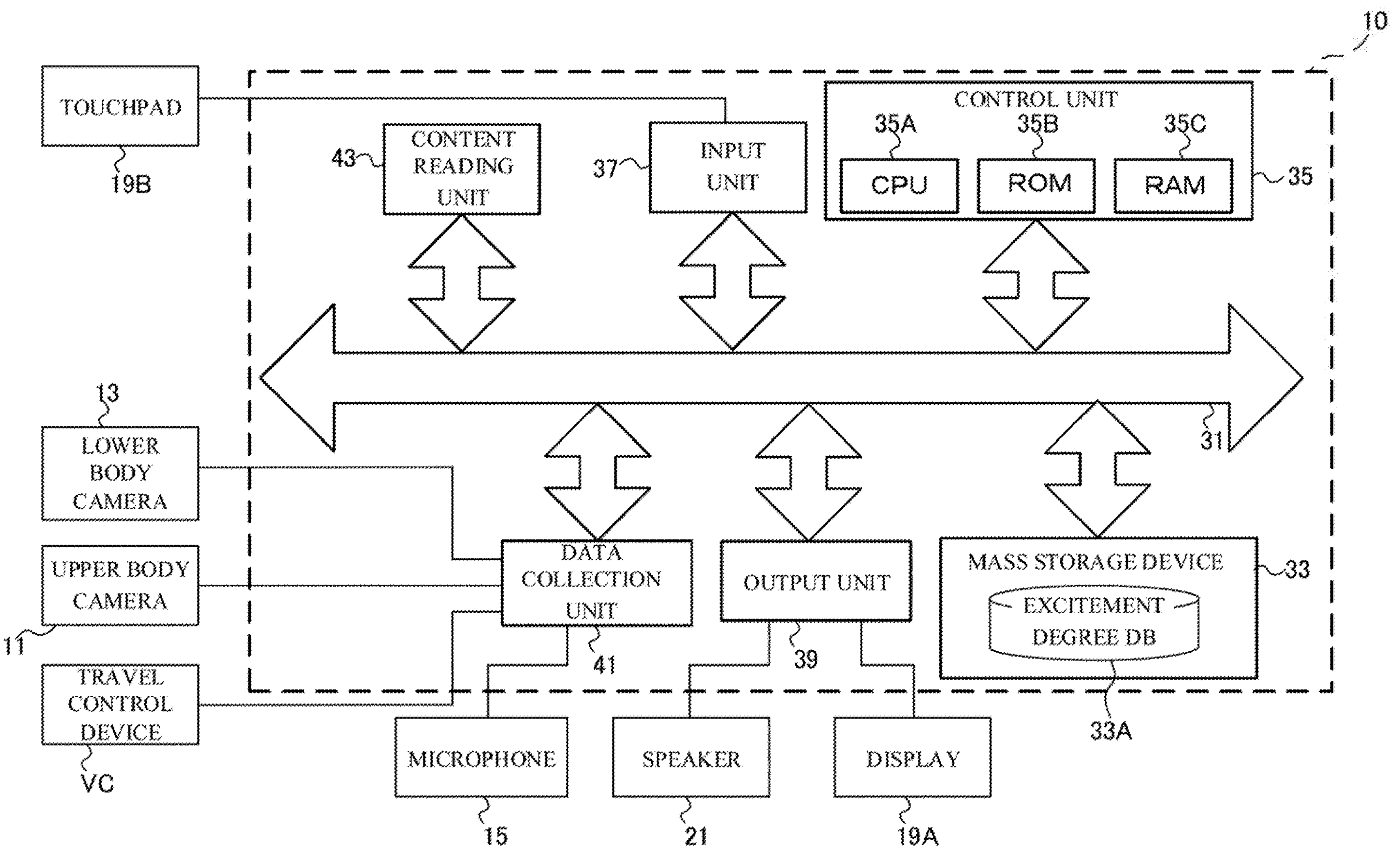
FIG. 2 is a block diagram illustrating an exemplary configuration of the excitement degree control device as Embodiment 1 of the present invention.

FIG. 2 illustrates the configuration of the excitement degree control device 10. For example, the excitement degree control device 10 is a device where a mass storage device 33, a control unit 35, an input unit 37, an output unit 39, a data collection unit 41, and a content reading unit 43 collaborate via a system bus 31.

The mass storage device 33 includes, for example, a hard disk drive, a solid state drive (SSD), a flash memory, and stores various programs, such as an operating system, software for a terminal, and the like. The various programs may be obtained from another server device and the like via a network, or may be recorded in a recording medium and read via various drive devices. That is, the various programs (including a program for executing a process in the excitement degree control device 10 described later) stored in the mass storage device 33 can be transmitted via the network, or can be recorded in a computer readable recording medium and transferred.

The control unit 35 includes a Central Processing Unit (CPU) 35A, a Read Only Memory (ROM) 35B, a Random Access Memory (RAM) 35C, and the like, and functions as a computer. Then, the CPU 35A reads the various programs stored in the ROM 35B and the mass storage device 33 and executes them, thereby ensuring various functions.

The input unit 37 is an interface unit that communicatively connects the excitement degree control device 10 to the touchpad 19B. The excitement degree control device 10 can receive the signal that indicates the input operation to the touchpad 19B via the input unit 37. The input unit 37 can be also an interface unit that communicatively connects the excitement degree control device 10 to the microphone 15. In this case, the excitement degree control device 10 can receive a sound input signal on a sound input operation by the user from the microphone 15 via the input unit 37.

The output unit 39 is communicatively connected to the display 19A and the speaker 21, and can transmit a video or image signal to the display 19A to display it or transmit a sound signal to the speaker 21 to output a sound.

A data collection unit 41 is an interface unit that communicatively connects the excitement degree control device 10 to the upper body camera 11, the lower body camera 13, and the microphone 15. The excitement degree control device 10 receives the video signal from the upper body camera 11 and the lower body camera 13 via the data collection unit 41.

The excitement degree control device 10 receives the sound signal from the microphone 15 via the data collection unit 41. The control unit 35 can calculate a movement feature amount, such as a movement amount of each part of a driver's body in a movement of the driver of an automobile to which the excitement degree control device 10 is mounted, from the video signal and the sound signal received via the data collection unit 41.

For example, the control unit 35 can calculate the movement feature amount based on a magnitude of the movement of the occupant of the automobile M based on the video signal from the upper body camera 11 and the lower body camera 13. The movement feature amount is a value where, for example, a preliminarily set maximum movement amount of each part of the body is assumed to 1, and a detected movement amount of each part of the body is normalized so as to become a value between 0 and 1. In this embodiment, as one example, image processing is performed, and the movement feature amount is calculated using only the movement amounts of a head, hands, and feet of the driver of the automobile M.

For example, the control unit 35 can calculate a sound feature amount based on the magnitude and the like of the sound of the occupant of the automobile M based on the sound input from the microphone 15. The sound feature amount is a value where, for example, a preliminarily set maximum sound is assumed to 1, and an input sound is normalized so as to become a value between 0 and 1. In this embodiment, as one example, the sound feature amount is calculated using a sound obtained by extracting only the sound of the driver of the automobile M as the input sound.

These calculated sound feature amount and movement feature amount are saved in an excitement degree database (excitement degree storage DB) 33A in the mass storage device 33.

The data collection unit 41 is also an interface that communicatively connects the excitement degree control device 10 to a travel control device VC of the automobile M to which the excitement degree control device 10 is mounted. The travel control device VC is a device that manages a travel control of the automobile M. In this embodiment, the travel control device VC determines whether a manual drive control is performed to the automobile M or an automatic drive control at any level of levels 1 to 5 is performed.

In this embodiment, the travel control device VC can transmit control information of whether the automobile M currently travels under the manual drive control or under the automatic drive control at any automatic driving level of the levels 1 to 5 to the excitement degree control device 10 via the data collection unit 41. The state of the manual drive control is defined as the automatic driving level 0.

When change of the drive control mode of the automobile M is scheduled, the travel control device VC can transmit the schedule to the excitement degree control device 10 via the data collection unit 41.

The content reading unit 43 may be a reading device (optical disk drive and the like) itself for an optical disk, such as a Compact Disc (CD), a DVD, or a Blu-ray Disc (BD), or may be communicatively connected to them. The content reading unit 43 may be an interface with a digital medium, for example, a USB terminal or a wireless communication device, such as a Wi-Fi communication device or a Bluetooth communication device. That is, the excitement degree control device 10 can obtain content data from outside via the content reading unit 43.

The control unit 35 can play the content data read from outside via the content reading unit 43 and display a video or an image (hereinafter simply referred to as video) of the content on the display 19A via the output unit 39. The control unit 35 can play the content data read from outside via the content reading unit 43 and cause the speaker 21 to generate sounds including the voice and the audio of the content.

[Operation as Excitement Degree Storage Device]

The following describes an operation when the excitement degree control device 10 functions as an excitement degree storage device. The excitement degree control device 10 when functioning as the excitement degree storage device plays the content, accepts an input of an evaluated excitement degree, which is an evaluation of an excitement degree of the driver of the automobile M during the playback of the content by the driver, and obtains it. In the following description, the evaluated excitement degree by the driver (hereinafter also referred to as user) and an actual excitement degree as an actual excitement degree of the driver are set to three levels of 1 to 3. The automatic driving level in the following description is, for example, an automatic driving level defined by Japanese Government or U.S. National Highway Traffic Safety Administration (NHTSA).

The excitement degree control device 10 when functioning as the excitement degree storage device obtains an action feature amount of the driver during the playback of the content and the evaluated excitement degree of the driver at the detection of the action feature amount. The excitement degree control device 10 aggregates the detected action feature amounts of the driver for each level of the evaluated excitement degree at the detection of the action feature amount. Then, the excitement degree control device 10 calculates reference values as the feature amounts corresponding to the respective levels of the excitement degree, such as average values of the action feature amounts at the respective levels of the excitement degree, from feature values aggregated for the respective levels of the evaluated excitement degree. The excitement degree control device 10 stores the respective levels of the excitement degree and the feature amounts corresponding to the respective levels of the excitement degree in association.

When the level of the actual excitement degree as the actually excited degree of the driver is determined from the action feature amount of the driver of the automobile M, the determination also can be made using a preliminarily determined reference value. However, by using the reference value calculated by aggregating the action feature amounts for each level of the evaluated excitement degree of the driver of the automobile M, the level of the actual excitement degree of the driver can be estimated or determined while adding a personal feature of the action of the driver of the automobile M. That is, by using the calculated reference value, the level of the excitement degree of the driver can be determined with more accuracy from the action feature amount of the driver of the automobile M.

The excitement degree control device 10 can provide the reference value of the feature amount conducive to the accurate determination of the level of the excitement degree of the driver.

[Exemplary Operation Routine for Operation as Excitement Degree Storage Device]

The following describes an exemplary operation routine of the excitement degree control device 10 when functioning as the excitement degree storage device.

Figure 3:
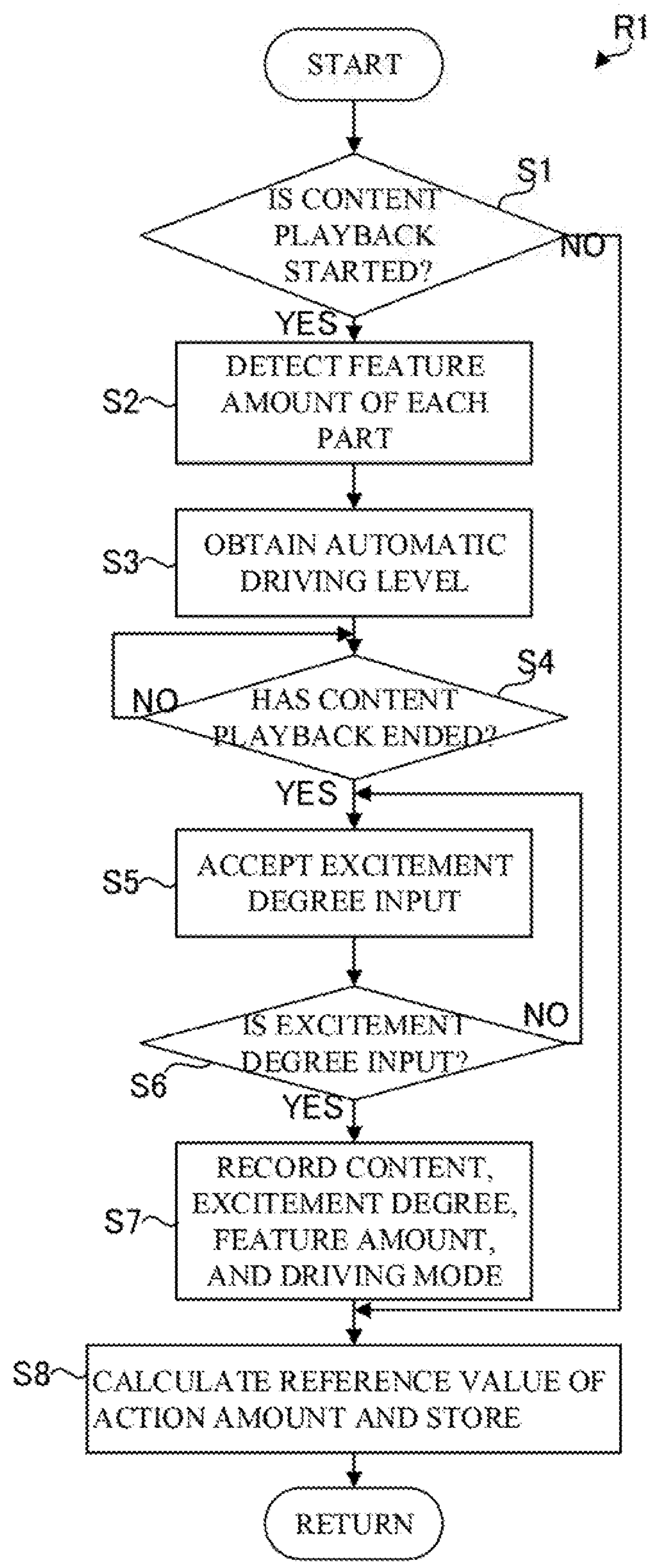
FIG. 3 is a flowchart of an operation routine of the excitement degree control device as Embodiment 1 of the present invention.

FIG. 3 is a drawing illustrating an excitement degree storing routine R1 as one example of the operation routine. The excitement degree storing routine R1 is repeatedly executed when, for example, the excitement degree control device 10 is turned on.

When the excitement degree storing routine R1 is started, the control unit 35 determines whether the playback of the content is started or not at first (Step S1). In Step S1, when the playback of the content is determined not to be started (Step S1: NO), the routine R1 ends.

For example, the playback of the content is started by the control unit 35 when the driver and the like performs a playback operation of the content via the touchpad 19B. For the playback of the content, the content read from the content reading unit 43 may be played, or the content saved in the mass storage device 33 may be played.

In Step S1, when the playback of the content is determined to be started (Step S1: YES), the control unit 35 obtains the action feature amount including the movement feature amount and the sound feature amount of the driver (Step S2). For example, the control unit 35 detects and obtains the action feature amounts of the driver from the video obtained from the upper body camera 11 and the lower body camera 13 and the sound obtained from the microphone 15. In this Step S1, the control unit 35 functions as the feature amount detection unit.

In this obtaining of the action feature amounts, for example, the above-described movement feature amount regarding the movement of the driver may be obtained through calculation of motion capture of the movements of the respective parts of the driver's body from the video obtained from the upper body camera 11 and the lower body camera 13.

When Step S2 ends, the control unit 35 obtains the automatic driving level (Step S3). As described above, the automatic driving level can be obtained from the travel control device VC via the data collection unit 41.

When Step S3 ends, the control unit 35 determines whether the playback of the content has ended or not (Step S4). In Step S4, when the playback of the content is determined not to have ended (Step S4: NO), the control unit 35 repeatedly executes Step S4.

In Step S4, when the playback of the content is determined to have ended (Step S4: YES), the control unit 35 waits for an input of the evaluated excitement degree from the driver (Step S5). For this waiting for input of the evaluated excitement degree, options of the level of the evaluated excitement degree may be indicated on the display 19A, thereby prompting the driver to input the evaluated excitement degree to the touchpad 19B. In this Step S5, the control unit 35 functions as an excitement degree obtaining unit.

After executing Step S5, the control unit 35 determines whether the evaluated excitement degree is input or not (Step S6). This determination can be made by whether the level of the evaluated excitement degree is selected via the touchpad 19B or not. In Step S6, when the evaluated excitement degree is determined not to be input (Step S6: NO), the control unit 35 executes Step S5 again and waits for the input of the evaluated excitement degree.

In Step S6, when the evaluated excitement degree is determined to be input (Step S6: YES), the control unit 35 accumulates the played content and the obtained evaluated excitement degree, automatic driving level, and action feature amount as excitement degree data in the excitement degree database 33A (Step S7). In this Step S7, the control unit 35 functions as a feature amount storage unit.

FIG. 4 illustrates an excitement degree data table T1 as one example of the excitement degree data accumulated in the excitement degree database 33A. In the excitement degree data table T1 illustrated in FIG. 4, as one example, a data ID is assigned to each piece of the excitement degree data, and the content and the automatic driving level, the evaluated excitement degree, and each of the feature amounts when the content is played are arranged from left in this order. In the excitement degree data table T1, the automatic driving levels of 3 or more are not distinguished. This is because, for example, a degree of freedom of the body of the driver does not vary in the automatic driving levels of 3 or more, and the action feature amounts are considered not to be different in tendency.

When Step S7 ends, the control unit 35 aggregates the excitement degree data saved in the excitement degree database 33A after the addition of the excitement degree data in Step S6. Then, the reference value of the feature amount usable for a determination criterion of the above-described actual excitement degree is calculated, and this is saved in the excitement degree database 33A (Step S8).

The reference value usable for the determination criterion of the actual excitement degree may be an average value, which is obtained for each part, of the action feature amounts associated with the same evaluated excitement degree. For example, in the excitement degree data table T1 illustrated in FIG. 4, the reference values corresponding to the level 1 of the evaluated excitement degree may be obtained by calculating the average values of the respective feature amounts associated with the data ID1, ID3, ID7, . . . , which are data having the same evaluated excitement degree.

FIG. 5 illustrates a reference value table T2 as one example of reference value data saved in the excitement degree database 33A. As illustrated in the reference value table T2, the reference values of the feature amounts of the respective parts of the body and the reference values of the feature amounts of the voices are saved corresponding to the respective levels of the excitement degree, that is, associated with the respective levels of the excitement degree.

Thus, in the excitement degree control device 10 that functions as the excitement degree storage device described above, the reference values of the respective feature amounts used for the criteria for determining, which level of the excitement degree the driver is in, are stored for respective levels of the excitement degree. By using the reference values, the accurate determination of the actual excitement degree from the feature amount of the driver in consideration of a driver's habit in action is facilitated. That is, the excitement degree control device 10 that functions as the excitement degree storage device described above can provide the reference value conducive to the accurate determination of the actual excitement degree in consideration of the driver's habit in action.

When the excitement degree is determined using the reference values, for example, a set of reference feature amounts most approximate to the respective feature amounts of the driver calculated from the video signal obtained from the upper body camera 11 and the lower body camera 13 and the sound signal obtained from the microphone 15 is determined. Then, the level of the actual excitement degree of the driver may be determined to be the level of the excitement degree associated with the set of the reference feature amounts.

In the above description, the reference values of the respective feature amounts are calculated for respective levels of the excitement degree with the classification by the excitement degree level alone. However, the degree of freedom of the driver's body differs depending on the automatic driving level in some cases.

For example, at the automatic driving level 0, since the driver needs to manually perform every operation relating to the travel of the automobile, the driver cannot release the hand from the steering wheel so much, and cannot release the feet from the proximity of the accelerator and the brake. Meanwhile, at the automatic driving level 3 or more, since steering and acceleration/deceleration at on are automated, the driver can relatively freely move the hand.

To calculate the reference value of the feature amount in consideration of the degree of freedom of the body depending on the difference of the automatic driving level, the feature amounts may be aggregated for each condition of the same excitement degree level and the same automatic driving level, thus calculating and save the reference values of the respective feature amounts.

FIG. 6 illustrates a reference value table T3 as one example of the reference value data saved in the excitement degree database 33A. As illustrated in the reference value table T3, the reference feature amounts may be saved in association with each of combinations of the excitement degree level and the automatic driving level.

Thus, by further subdividing the reference value used for the determination criterion of the excitement degree by the automatic driving level, the reference value conducive to further accurate determination can be provided.

The excitement degree control device 10 may function as an excitement suppression device that determines the excitement degree using the reference value, and performs a suppression operation to suppress the excitement degree of the driver when the excitement degree is determined to exceed a predetermined threshold. At this time, the excitement degree control device 10 can obtain the action feature amount of the driver in a predetermined period of time and determine the excitement degree of the driver based on the action feature amount and the reference value.

[Operation as Excitement Degree Determination Device]

The following describes an operation of the excitement degree control device 10 when functioning as an excitement degree determination device. In the following description, the excitement degree is described to be high as the action feature amount increases. The excitement degree control device 10 when functioning as the excitement degree determination device obtains the action feature amounts of the respective parts of the body of the driver of the automobile M and drive control information of the automobile M when the action feature amounts are obtained. The drive control information includes the automatic driving level. Then, the level of the excitement degree of the driver is determined based on the obtained action feature amount and drive control information.

The automatic driving level changes dependency of the travel control of the automobile M on the driver depending on the level. Therefore, the automatic driving level can be also referred to as dependency information on the dependency of the travel control of the automobile M on the driver.

It is predicted that the driver has different degree of freedom of the movement of the body depending on the level of the automatic driving. Therefore, by adding the automatic driving level to the determination of the excitement degree by the action feature amount, the excitement degree of the driver can be accurately determined.

In the determination of the level of the excitement degree, the excitement degree control device 10 may correct the action feature amount based on the automatic driving level and determine the excitement degree level using the corrected value. That is, a correction coefficient to the action feature amount may be individually set for each automatic driving level.

The correction of the action feature amount may be individually performed for each action feature amount of each part of the driver's body. That is, the correction coefficient to the action feature amount may be individually set for each action feature amount of each part of the driver's body.

The degree of freedom of the movement of each part of the driver's body is different depending on the condition of the automatic driving. For example, when the steering needs to be manually performed, the degree of freedom of the movement of the upper body is low. For example, when the acceleration/deceleration needs to be manually performed, the degree of freedom of the movement of the lower body is low. By performing the correction of the action feature amount based on the automatic driving level for each part of the driver's body, the excitement degree level can be determined while adding the degree of freedom of each part of the driver's body.

The excitement degree control device 10 may change an excitement degree determination reference value as a reference value used for the determination of the excitement degree level based on the automatic driving level without the correction of the action feature amount.

The excitement degree control device 10 may determine the excitement degree level to be low as the automatic driving level increases. For example, in the determination of the excitement degree level, the excitement degree control device 10 may decrease the value after the action feature amount correction as the automatic driving level increases. In the determination of the excitement degree level, the excitement degree control device 10 may increase the reference value used for the excitement degree level determination as the automatic driving level increases.

Usually, the degree of freedom of the movement of the driver's body increases as the automatic driving level increases. Therefore, as the automatic driving level decreases, that is, as the dependency on the driver increases, the excitement degree level is likely to be determined to be high, thus ensuring appropriate determination of the excitement degree level.

[Exemplary Operation Routine for Operation as Excitement Degree Determination Device]

The following describes an exemplary operation routine of the excitement degree control device 10 when functioning as the excitement degree determination device.

Figure 7:
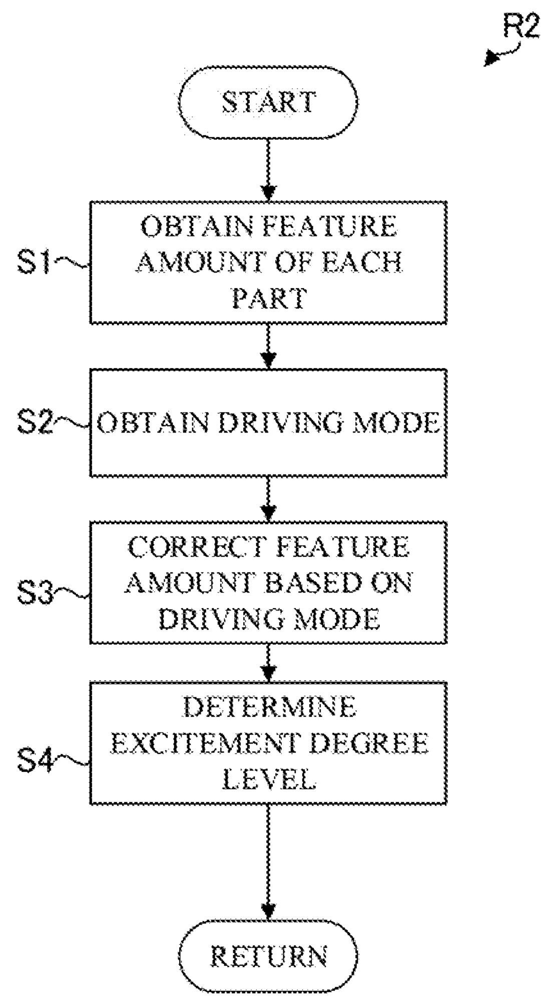
FIG. 7 is a flowchart of an operation routine of the excitement degree control device as Embodiment 1 of the present invention.

FIG. 7 is a drawing illustrating an excitement degree determination routine R2 as one example of the operation routine. The excitement degree determination routine R2 is repeatedly executed when, for example, the excitement degree control device 10 is turned on.

When the excitement degree determination routine R2 is started, the control unit 35 detects and obtains the action feature amount including the movement feature amount and the sound feature amount of the driver at first (Step S1). In this Step S1, the control unit 35 functions as the feature amount detection unit.

For example, the control unit 35 obtains the action feature amounts of the driver from the video obtained from the upper body camera 11 and the lower body camera 13 and the sound obtained from the microphone 15. In this obtaining of the action feature amounts, for example, the above-described movement feature amount regarding the movement of the driver may be obtained through calculation of motion capture of the movements of the respective parts of the driver's body from the video obtained from the upper body camera 11 and the lower body camera 13.

When Step S1 ends, the control unit 35 obtains the automatic driving level (Step S2). As described above, the automatic driving level can be obtained from the travel control device VC via the data collection unit 41. In this Step S2, the control unit 35 functions as a travel control information obtaining unit.

When Step S2 ends, the control unit 35 corrects each of the action feature amounts obtained in Step S1 based on the automatic driving level (Step S3). For example, the correction may be performed by multiplying the respective action feature amounts by coefficients that increase as the automatic driving level increases. In other words, as the number of operations performed by the driver for the travel of the automobile M increases, that is, as the degree of dependency of the travel control of the automobile M on the driver becomes higher, the coefficient by which the action feature amounts are each multiplied may be increased.

As described above, different correction values may be set to the respective action feature amounts. For example, in the case of the automatic driving level 1 or 2, the action feature amount of the hand may be multiplied by 0.7 as the correction value without the correction of the other action feature amounts when the steering is automated, or the feet may be multiplied by 0.8 as the correction value without the correction of the other action feature amounts when the acceleration/deceleration is automated. In the case of the automatic driving level 3 or more, every movement feature amount may be multiplied by 0.5 as the correction value without the correction of the sound feature amount.

When Step S3 ends, the control unit 35 determines the excitement degree of the driver using the correction value obtained in Step S3 (Step S4). In this Step S4, the control unit 35 functions as an excitement degree determination unit. The excitement degree determination may be performed based on a preliminarily set reference value. The excitement degree determination may be performed based on the reference value of the action feature amount calculated and saved by the excitement degree control device 10 when functioning as the excitement degree storage device.

Thus, according to the excitement degree control device 10 when functioning as the excitement degree determination device described above, the excitement degree can be determined while adding the difference in automation level or automatic driving level. Specifically, for example, the determination of the excitement degree of the driver based on the action feature amount can be performed while adding the degree of physical freedom of the driver that differs depending on the automation level. Therefore, the excitement degree of the driver can be accurately determined.

While the action feature amounts are each corrected in Step S3 in the description of the excitement degree determination routine R2 described above, the action feature amounts do not need to be each corrected. In this case, the reference value preliminarily set for the determination of the excitement degree level may be corrected based on the automatic driving level of the automobile M or the aspect of the automatic drive control, such as the acceleration/deceleration automatic control or the steering automatic control.

[Operation as Excitement Degree Suppression Device (Pattern 1)]

The following describes an exemplary operation of the excitement degree control device 10 when functioning as an excitement degree suppression device. In the following description, the excitement degree is described to be high as the action feature amount increases. The excitement degree control device 10 when functioning as the excitement degree suppression device obtains the action feature amounts of the respective parts of the body of the driver of the automobile M and the automatic driving level of the automobile M when the action feature amounts are obtained.

The excitement degree control device 10 determines the excitement degree of the driver based on the obtained action feature amounts. Then, the excitement degree control device 10 determines whether the determined excitement degree exceeds an excitement degree threshold, which is determined based on the current automatic driving level of the automobile M, or not, and executes an operation to suppress the excitement degree of the driver when the excitement degree threshold is determined to be exceeded.

The operation to suppress the excitement degree may be, for example, an operation to play a video content or a sound or audio content that reduces the excitement degree of the driver, that is, calms the driver via the display 19A or the speaker 21.

In the excitement degree control device 10, the excitement degree threshold may be set low as the automatic driving level becomes low, that is, the dependency of the travel control of the automobile M on the driver becomes high. The determination whether the excitement degree threshold is exceeded or not may be made based on whether an average value of the action feature amounts of the driver exceeds a predetermined threshold or not, or whether one or a plurality of individual action feature amounts exceed thresholds set for the respective individual action feature amounts or not.

According to the excitement degree control device 10 that functions as the excitement degree suppression device, the excitement degree of the driver is appropriately controlled corresponding to the automatic driving level, that is, corresponding to the dependency of the travel control of the automobile M on the driver, thereby ensuring leading the driver to the state appropriate for the control.

[Exemplary Operation Routine for Operation as Excitement Degree Suppression Device (Pattern 1)]

Figure 8:
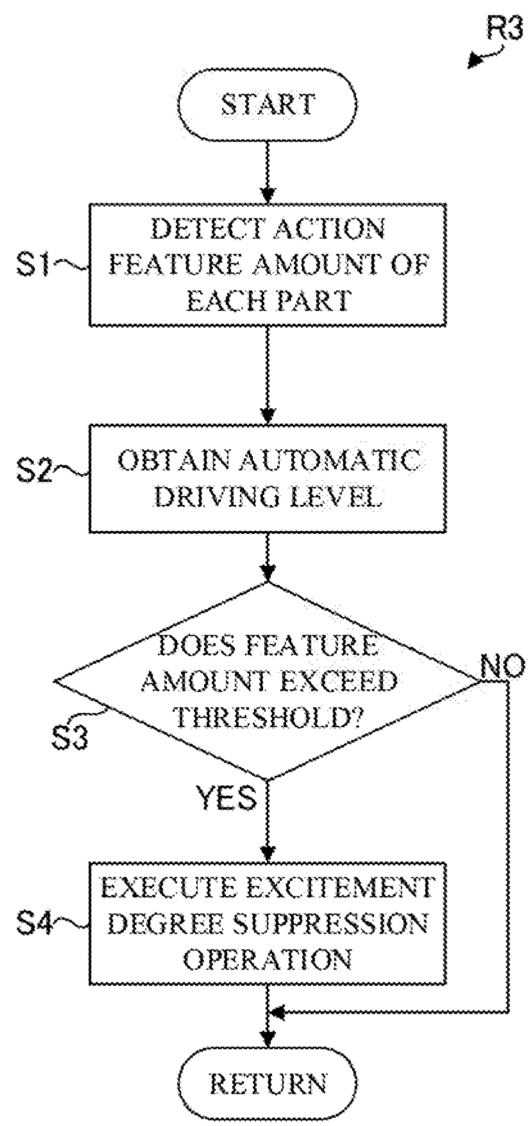
FIG. 8 is a flowchart of an operation routine of the excitement degree control device as Embodiment 1 of the present invention.

The following describes an exemplary operation routine of the excitement degree control device 10 when functioning as the excitement degree suppression device. FIG. 8 is a drawing illustrating an excitement degree suppression routine R3 as one example of the operation routine. The excitement degree suppression routine R3 is repeatedly executed when, for example, the excitement degree control device 10 is turned on.

When the excitement degree suppression routine R3 is started, the control unit 35 obtains the action feature amount including the movement feature amount and the sound feature amount of the driver as the excitement degree at first (Step S1). For example, the control unit 35 obtains the action feature amounts of the driver from the video obtained from the upper body camera 11 and the lower body camera 13 and the sound obtained from the microphone 15. In Step S1, the control unit 35 functions as an excitement degree obtaining unit.

In this obtaining of the action feature amounts, for example, the above-described movement feature amount regarding the movement of the driver may be obtained through calculation of motion capture of the movements of the respective parts of the driver's body from the video obtained from the upper body camera 11 and the lower body camera 13.

When Step S1 ends, the control unit 35 obtains the automatic driving level (Step S2). As described above, the automatic driving level can be obtained from the travel control device VC via the data collection unit 41. In this Step S2, the control unit 35 functions as a travel control information obtaining unit.

When Step S2 ends, the control unit 35 determines whether the excitement degree obtained in Step S1 exceeds an excitement degree threshold determined corresponding to the automatic driving level or not (Step S3). In this Step S3, the control unit 35 functions as an excitement degree determination unit. In this determination, the excitement degree may be determined to exceed the excitement degree threshold when the average of the action feature amounts of the respective parts of the body obtained in Step S1 exceeds a feature value threshold determined corresponding to the automatic driving level.

In this determination, the excitement degree may be determined to exceed the excitement degree threshold when one or a plurality of the action feature amounts of the respective parts of the body obtained in Step S1 exceed the feature amount thresholds determined for the respective action feature amounts of the respective parts of the body corresponding to the automatic driving level.

In Step S3, after the excitement degree is determined not to exceed the threshold (Step S3: NO), the routine ends. In Step S3, when the excitement degree is determined to exceed the threshold (Step S3: YES), the control unit 35 executes an excitement degree suppression operation to suppress the excitement degree of the driver (Step S4). In this Step S4, the control unit 35 functions as an excitement suppression unit. As described above, the excitement degree suppression operation may be, for example, an operation to play a content that reduces the excitement degree of the driver, that is, calms the driver via the display 19A or the speaker 21, or may be an operation to play a content with a low excitement degree stored in, the excitement degree storage device.

In the description of the excitement degree suppression routine R3 described above, in Step S3, whether the excitement degree exceeds the excitement degree threshold or not is determined using the feature amount threshold determined corresponding to the automatic driving level.

However, the feature amount threshold may be determined corresponding to not only the automatic driving level but also the aspect of the automatic drive control. For example, when the steering control is automated, since the driver does not need to operate the steering wheel and has a high degree of freedom of the movement of the hand, the threshold of the feature amount of the movement of the hand may be increased or eliminated. For example, when the acceleration/deceleration control is automated, since the driver does not need to operate the accelerator or the brake and has a high degree of freedom of the movement of the foot, the threshold of the feature amount of the movement of the foot may be increased or eliminated.

[Operation as Excitement Degree Suppression Device (Pattern 2)]

The following describes an exemplary operation of the excitement degree control device 10 when functioning as the excitement degree suppression device. In the following description, the excitement degree is described to be high as the action feature amount increases.

The excitement degree control device 10 when functioning as the excitement degree suppression device obtains travel control mode transition information (hereinafter also referred to simply as mode transition information) sent from the travel control device VC when transition of the travel control mode where the dependency on the driver differs, for example, transition of the automatic driving level, is performed. The mode transition information includes, for example, information on the current travel control mode and the travel control mode after the transition. That is, the mode transition information is information on the transition of the travel control mode.

When the mode transition information is received, that is, obtained, the excitement degree control device 10 determines whether the dependency on the driver in the travel control mode after the transition is higher than that in the travel control mode before the transition or not. Specifically, for example, whether the automatic driving level after the transition is lower in level than the automatic driving level before the transition or not is determined.

When the dependency on the driver in the travel control mode after the transition is determined to be higher than that of the travel control mode before the transition, the excitement degree control device 10 executes an operation to suppress the excitement degree of the driver. The operation to suppress the excitement degree may be, for example, an operation to play a video content or a sound or audio content that reduces the excitement degree of the driver, that is, calms the driver via the display 19A or the speaker 21.

The excitement degree control device 10 may obtain the current excitement degree of the driver, determine whether to exceed the drive control mode after the transition, for example, the excitement degree threshold determine based on the automatic driving level or not, and execute the operation to suppress the excitement degree of the driver when the excitement degree threshold is determined to be exceeded. The excitement degree of the driver may be calculated based on the action feature amount of the driver.

The excitement degree control device 10 may perform the operation having a large suppression effect of the excitement degree as a difference between the excitement degree and the excitement degree threshold increases when the obtained excitement degree of the driver exceeds the excitement degree threshold. The excitement degree control device 10 may perform the operation having a large suppression effect of the excitement degree as a time period to the transition of the travel control mode becomes short.

The suppression effect of the excitement degree may be increased as a melody of a musical composition to be played becomes calm, specifically, a pitch of the musical composition to be played becomes slow.

According to the excitement degree control device 10 that functions as the excitement degree suppression device, the excitement degree of the driver is controlled when the travel control mode is transitioned to the mode where the dependency on the driver is higher, thereby ensuring leading the driver to the state appropriate for the control.

[Exemplary Operation Routine for Operation as Excitement Degree Suppression Device (Pattern 2)]

Figure 9:
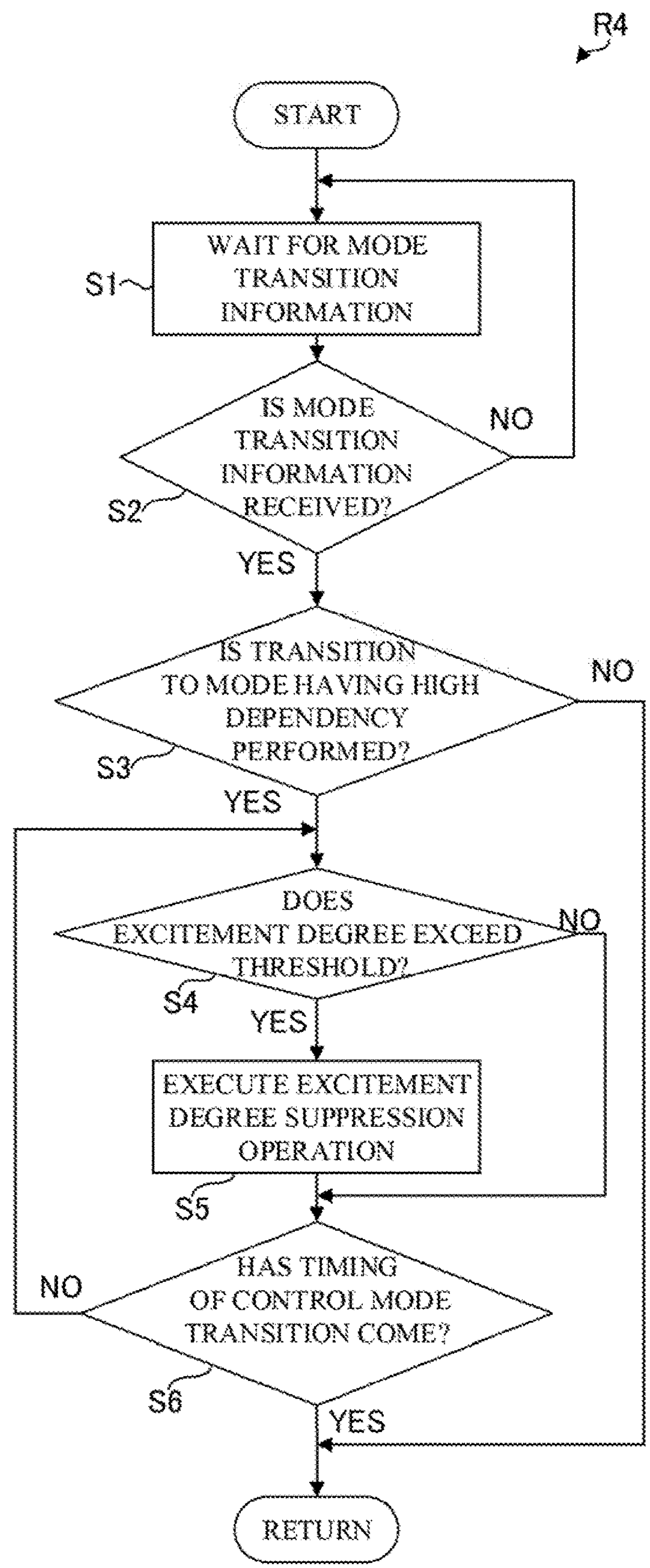
FIG. 9 is a flowchart of an operation routine of the excitement degree control device as Embodiment 1 of the present invention.

The following describes an exemplary operation routine of the excitement degree control device 10 when functioning as the excitement degree suppression device. FIG. 9 is a drawing illustrating an excitement degree suppression routine R4 as one example of the operation routine. The excitement degree suppression routine R4 is repeatedly executed when, for example, the excitement degree control device 10 is turned on.

When the excitement degree suppression routine R4 is started, the control unit 35 waits for arrival of the mode transition information at first (Step S1). The mode transition information is sent from the travel control device VC when the travel control device VC determines the travel control mode to be transitioned. For example, this determination may be made based on whether the automatic driving level to be allowed is different between a current point and a point to be reached soon or not by obtaining position information from the UPS receiver 17 by the travel control device VC.

When Step S1 ends, the control unit 35 determines whether the mode transition information arrives and is received or not (Step S2). In Steps S1 and S2, the control unit 35 functions as a mode transition information obtaining unit. In Step S2, when the mode transition information is determined not to have been received yet (Step S2: NO), the control unit 35 continues the execution of Step S1 and waits for the arrival of the mode transition information.

In Step S2, when the mode transition information is determined to be received (Step S2: YES), the control unit 35 determines whether the travel control mode transitions to the mode with the high dependency on the driver or not (Step S3). In this determination, the travel control mode may be transitioned to the mode with the high dependency on the driver by that, for example, the automatic driving level after the transition is lower than the current driving level before the transition.

In Step S3, when the transition to the travel control mode with the high dependency on the driver is not determined (Step S3: NO), that is, the dependency on the driver is determined not to be different from that of the current control mode, or the dependency on the driver is determined to be decreased, the routine R4 ends.

In Step S3, when the transition to the travel control mode with the high dependency on the driver is determined (Step S3: YES), the control unit 35 determines whether the current excitement degree exceeds the excitement degree threshold determined by the travel control mode after the transition or not (Step S4).

In Step S4, for example, the control unit 35 obtains the action feature amounts of the respective parts of the body based on the information from the upper body camera 11, the lower body camera 13, or the microphone 15. Then, the excitement degree may be determined to exceed the excitement degree threshold when an average of the obtained action feature amounts of the respective parts exceeds a feature amount threshold determined corresponding to the travel control mode, for example, the automatic driving level.

In Step S4, the excitement degree may be determined to exceed the excitement degree threshold when one or a plurality of the obtained action feature amounts of the respective parts of the body exceed the feature amount thresholds determined for the respective action feature amounts of the respective parts of the body corresponding to the travel control mode, for example, the automatic driving level.

In Step S4, when the excitement degree is determined to exceed the threshold (Step S4: YES), the control unit 35 executes an excitement degree suppression operation to suppress the excitement degree of the driver (Step S5). In Steps S3 to 5, the control unit 35 functions as an excitement suppression unit. As described above, the excitement degree suppression operation may be, for example, an operation to play a content that reduces the excitement degree of the driver via the display 19A or the speaker 21.

When Step S5 ends or when the excitement degree is determined to exceed the threshold in Step S4 (Step S4: NO), the control unit 35 determines whether a timing of the transition of the drive control mode has come or not (Step S6). This determination may be performed by, for example, querying the travel control device VC about the timing of the transition of the drive control mode from the control unit 35.

In Step S6, when the timing of the control mode transition is determined to have come (Step S6: YES), the control unit 35 terminates the excitement degree suppression operation and the routine ends. In Step S6, when the timing of the control mode transition is determined not to have come yet (Step S6: NO), the control unit 35 executes Step S4 again, and continues the excitement degree suppression operation when the excitement degree still exceeds threshold.

Figure 10:
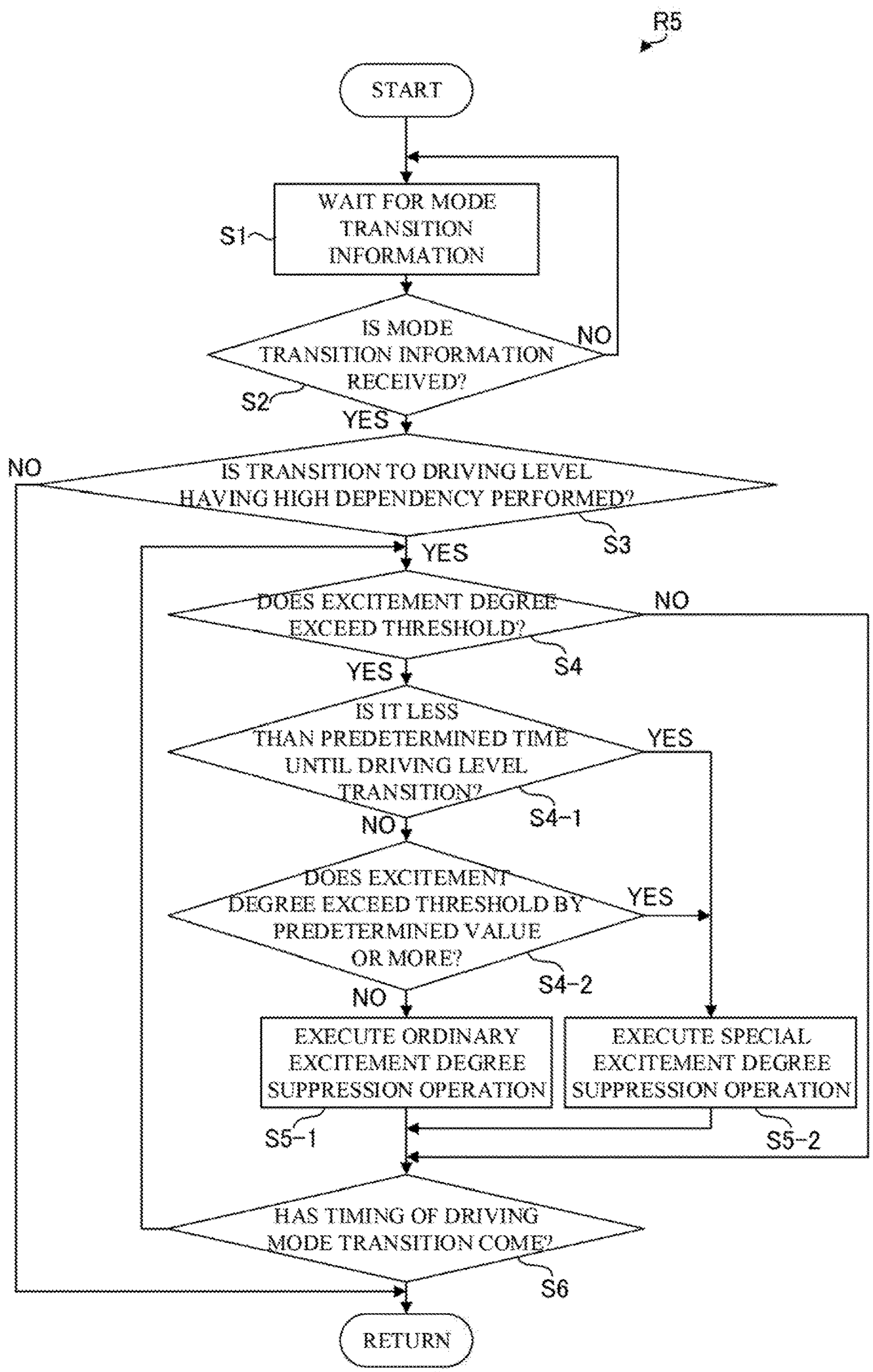
FIG. 10 is a flowchart of an operation routine of the excitement degree control device as Embodiment 1 of the present invention.

While the difference between the excitement degree and the excitement degree threshold or the time period to the transition of the travel control mode is not considered in the excitement degree suppression routine R4, they may be taken into consideration, FIG. 10 illustrates an excitement degree suppression routine R5 when the difference between the excitement degree and the excitement degree threshold or the time period to the transition of the travel control mode is considered. Since the excitement degree suppression routine R5 is only partially different in process from the excitement degree suppression routine R4, a description will be given of only the different part.

In the excitement degree suppression routine R5, when the excitement degree is determined to exceed the threshold in Step S4 (Step S4: YES), the control unit 35 determines whether the time period to the transition of the travel control mode is less than a predetermined time period (Step S4-1).

In Step S4-1, when the predetermined time period or more to the transition of the travel control mode is determined (Step S4-1: YES), the control unit 35 determines whether the difference between the current excitement degree of the driver and the excitement degree threshold determined depending on the travel control mode after the transition is the predetermined value or more or not (Step S4-2).

In Step S4-2, when the difference between the current excitement degree and the excitement degree threshold is determined to be the predetermined value or less (Step S4-2: NO), the control unit 35 executes the ordinary excitement degree suppression operation (Step S5-1). When the time period to the transition of the travel control mode is determined to be less than the predetermined time period (Step S4-1: YES) in Step S4-1, or the difference between the current excitement degree and the excitement degree threshold is determined to be the predetermined value or more (Step S4-2: YES) in Step S4-2, the control unit 35 executes a special excitement degree suppression operation (Step S5-2).

The special excitement degree suppression operation is an operation that provides a high effect to suppress (reduce) the excitement degree of the driver compared with the ordinary excitement degree suppression operation. For example, in the special excitement degree suppression operation, a music that has a melody further calm compared with that played in the ordinary excitement degree suppression operation may be played.

[Operation as Content Selection Device]

The following describes an exemplary operation of the excitement degree control device 10 when functioning as a content selection device.

The excitement degree control device 10 when functioning as the content selection device plays a content, such as a video or a sound, obtains the action feature amount of the driver during the playback of the content, saves it in association with content information as information of the content, and accumulates it.

When one content is played, the excitement degree control device 10 when functioning as the content selection device selects a next content as a content to be played next to the one content based on the saved content information and the action feature amount associated with it.

For example, the selection of the content is performed by selecting a content having a way of excitement close to a way of getting a rhythm or a way of excitement (hereinafter simply referred to as way of excitement) of the user with the playing one content. In the following description, it is determined that the one content and the other content is close in the way of excitement of the user when a degree of coincidence of the action feature amount of the user is high between the one content and the other content.

Accordingly, the excitement degree suppression device 10 performs the selection from the other contents based on the comparison between the action feature amount associated with the currently playing one content and the action feature amount associate with the other content. For example, the excitement degree suppression device 10 performs the selection from the other contents based on the comparison between the action feature amount associated with the playing one content and the action feature amount associated with the other content. Specifically, for example, the excitement degree control device 10 selects a content associated with the action feature amount having the high degree of coincidence with the action feature amount associated with the playing one content among the other contents.

The evaluation of the degree of coincidence of the action feature amount may be performed by an evaluation where the associated action feature amount is compared for each part of the body between the one content and the other content, and the degree of coincidence is high when a sum of the differences of the feature amounts is low.

The evaluation of the degree of coincidence of the action feature amount may be performed by an evaluation where a ratio of the action feature amounts (for example, head feature amount: hand feature amount: foot feature amount) of the respective parts of the body associated with the one content is compared with that of the action feature amounts of the respective parts of the body associated with the other content, and the degree of coincidence is high when a degree of approximation of the ratio values is high.

Thus, according to the excitement degree suppression device 10 that functions as the content selection device described above, by selecting the content having the way of excitement of the user close to that of the currently playing content as the content to be played next to the currently playing content, the content can be played without diminishing the excitement of the user. When the content to suppress the excitement degree is playing, a content to suppress the excitement degree can be subsequently played.

[Exemplary Operation Routine for Operation as Excitement Degree Storage Device]

The following describes an exemplary operation routine of the excitement degree control device 10 when functioning as the excitement degree storage device.

Figure 11:
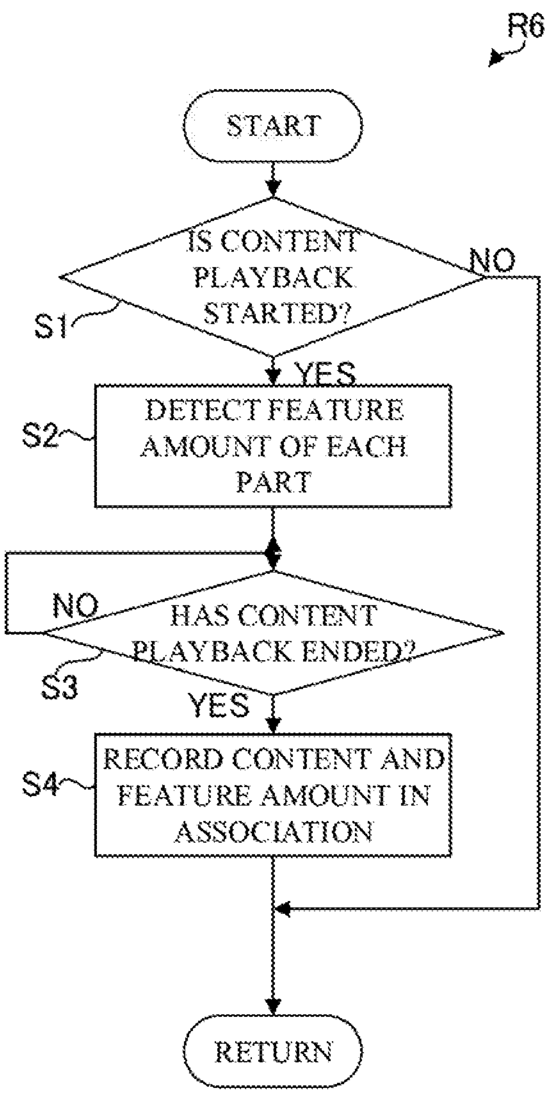
FIG. 11 is a flowchart of an operation routine of the excitement degree control device as Embodiment 1 of the present invention.

FIG. 11 is a drawing illustrating an excitement degree accumulating routine R6 as one example of the operation routine to accumulate the way of excitement of the user. The excitement degree accumulating routine R6 is repeatedly executed when, for example, the excitement degree control device 10 is turned on.

When the excitement degree accumulating routine R6 is started, the control unit 35 determines whether the playback of the content is started or not at first (Step S1). In Step S1, when the playback of the content is determined not to be started (Step S1: NO), the routine R6 ends.

In Step S1, when the playback of the content is determined to be started (Step S1: YES), the control unit 35 detects and obtains the action feature amount including the movement feature amount and the sound feature amount of the driver (Step S2). In this Step S2, the control unit 35 functions as the feature amount detection unit. For example, the control unit 35 obtains the action feature amounts of the driver from the video obtained from the upper body camera 11 and the lower body camera 13 and the sound obtained from the microphone 15.

In this obtaining of the action feature amounts, for example, the above-described movement feature amount regarding the movement of the driver may be obtained through calculation of motion capture of the movements of the respective parts of the driver's body from the video obtained from the upper body camera 11 and the lower body camera 13.

When Step S2 ends, the control unit 35 determines whether the playback of the content is terminated or not (Step S3). In Step S3, when the playback of the content is determined not to have ended (Step S3: NO), the control unit 35 repeatedly executes Step S3.

In Step S3, when the playback of the content is determined to have ended (Step S3: YES), the control unit 35 accumulates the played content and the action feature amount as the excitement degree data in the excitement degree database 33A (Step S4). In this Step S4, the control unit 35 functions as a storage unit.

Here, the data accumulated in the excitement degree database 33A may be, for example, data where the automatic driving level and the evaluated excitement degree are removed from the excitement degree data table T1 illustrated in FIG. 4 in the above description.

This, by the excitement degree accumulating routine R6, information including the content and the action feature amount associated with the content is accumulated.

Figure 12:
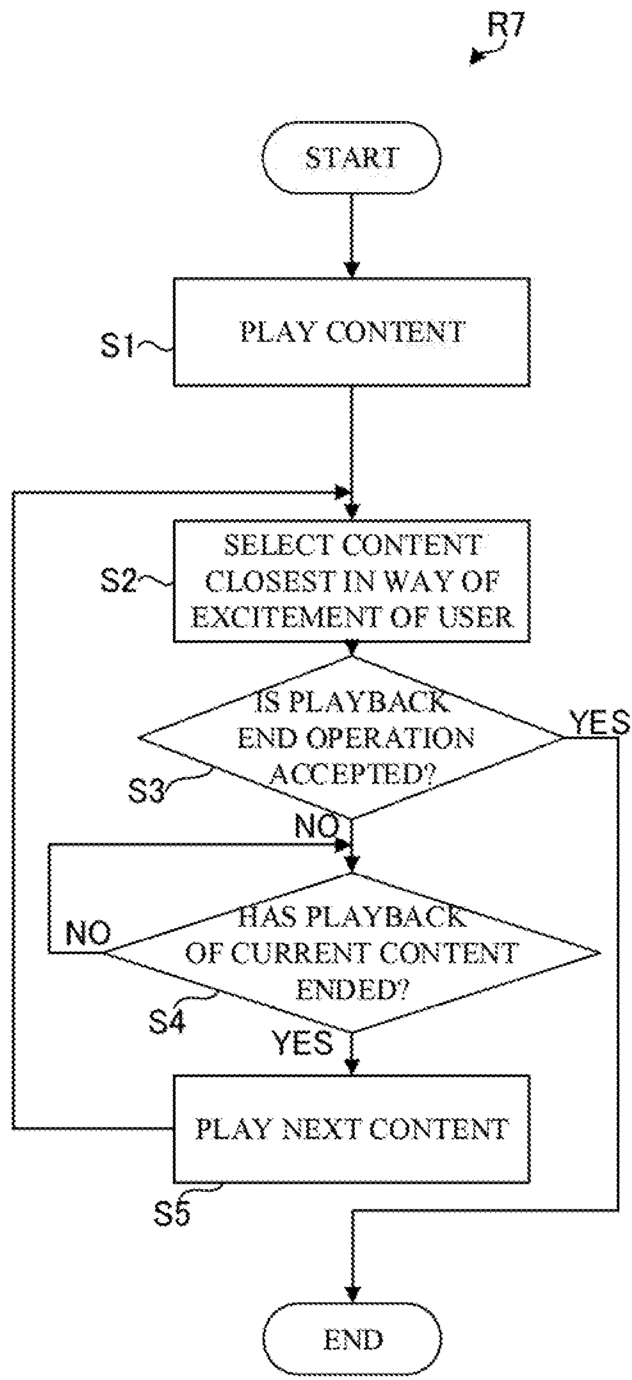
FIG. 12 is a flowchart of an operation routine of the excitement degree control device as Embodiment 1 of the present invention.

FIG. 12 is a drawing illustrating a content playing routine R7 where the content with which the user is excited in a way similar to that of the playing content is selected as the next content while the playback is performed. The content playing routine R7 may be started when, for example, a playback operation of the content is accepted from the user via the touchpad 19B and the like.

When the content playing routine is started, the control unit 35 starts the playback of the content at first (Step S1). In this Step S1, the control unit 35 functions as a content playing unit. When Step S1 ends, the control unit 35 selects a content where the way of excitement of the user is close to the way of excitement of the playing content (Step S2). In this Step S2, the control unit 35 functions as a content selection unit.

For example, this selection, the control unit 35 refers to the data saved in the excitement degree database 33A by the above-described excitement degree accumulating routine R6 at first, and reads out the action feature amount associated with the playing content. Then, the content associated with the action feature amount highest in degree of coincidence with the read action feature amount is selected as a next playback content to be played next.

After the end of Step S2, the control unit 35 determines whether a playback end operation is accepted from the user (Step S3). This determination may be determined by, for example, whether the playback end operation of the content is accepted from the user via the touchpad 19B and the like or not.

In Step S3, when the playback end operation is determined to be accepted (Step S3: YES), the routine R7 ends.

In Step S3, when the playback end operation is determined not to be accepted (Step S3: NO), the control unit 35 determines whether the currently playing content has ended (Step S4). In Step S4, when the currently playing content is determined not to have ended (Step S4: NO), the control unit 35 executes Step S4 again.

In Step S4, when the currently playing content is determined to have ended (Step S4: YES), the control unit 35 plays the next content selected in Step S2 (Step S5). After the end of Step S5, the control unit 35 executes Step S2 again.

According to the excitement degree control device 10 described in Embodiment 1, the excitement degree of the driver can be effectively controlled, thereby ensuring a support for driving of the driver.

The configuration, the routine, the format of the data, or the like of the excitement degree control device 10 in the above-described embodiment is merely an illustration, and can be selected or changed as necessary depending on the usage and the like.

DESCRIPTION OF REFERENCE SIGNS

10 Excitement degree control device
31 System bus
33 Mass storage device
35 Control unit

The invention claimed is:

1. A storage device comprising:

a feature amount detection unit that detects a feature amount regarding an action of an occupant of a moving body;

an excitement degree obtaining unit that obtains excitement degree information, the excitement degree information indicating an excitement degree of the occupant evaluated by the occupant when the feature amount is detected; and a feature amount storage unit that calculates a first corresponding feature amount based on the feature amount and the excitement degree information, and stores the first corresponding feature amount in association with a first excitement degree, the first corresponding feature amount being a feature amount corresponding to the first excitement degree of the excitement degree.

2. The storage device according to claim 1, further comprising:

an automatic driving level obtaining unit that obtains automatic driving level information, the automatic driving level information indicating an automatic driving level of the moving body when the feature amount is detected, wherein the feature amount storage unit calculates a second corresponding feature amount based on the feature amount, the excitement degree information, and the automatic driving level information, and stores the second corresponding feature amount in association with the first excitement degree and a first automatic driving level, the second corresponding feature amount being a feature amount corresponding to the first excitement degree and the first automatic driving level of the automatic driving level.

3. The storage device according to claim 1, wherein the feature amount detection unit detects the feature amount while a predetermined content is played.

4. An excitement suppression device comprising:

a feature amount detection unit that detects a feature amount regarding an action of an occupant of a moving body;

an excitement degree obtaining unit that obtains excitement degree information, the excitement degree information indicating an excitement degree of the occupant evaluated by the occupant when the feature amount is detected;

a feature amount storage unit that calculates a first corresponding feature amount based on the feature amount and the excitement degree information, and stores the first corresponding feature amount in association with a first excitement degree, the first corresponding feature amount being a feature amount corresponding to the first excitement degree of the excitement degree; and an excitement suppression unit that determines an excitement degree of the occupant in a predetermined period of time based on the feature amount and a first feature amount, and performs a suppression operation to suppress the excitement degree of the occupant when the determined excitement degree is determined to exceed a predetermined threshold, the feature amount being detected by the feature amount detection unit in the predetermined period of time, and the first feature amount being stored in the feature amount storage unit.

* * * * *